US010875986B2

(12) United States Patent
Humfeld et al.

(10) Patent No.: US 10,875,986 B2
(45) Date of Patent: *Dec. 29, 2020

(54) GRAPHENE FIBER FOR AEROSPACE COMPOSITES

(71) Applicant: The Boeing Company, Chicago, IL (US)

(72) Inventors: Keith Daniel Humfeld, Federal Way, WA (US); Kenneth H. Griess, Kent, WA (US)

(73) Assignee: The Boeing Company, Chicago, IL (US)

( * ) Notice: Subject to any disclaimer, the term of this patent is extended or adjusted under 35 U.S.C. 154(b) by 662 days.

This patent is subject to a terminal disclaimer.

(21) Appl. No.: 14/589,036

(22) Filed: Jan. 5, 2015

(65) Prior Publication Data
US 2016/0194482 A1 Jul. 7, 2016

(51) Int. Cl.
*C08K 9/04* (2006.01)
*C08J 5/24* (2006.01)
(Continued)

(52) U.S. Cl.
CPC .............. *C08K 9/04* (2013.01); *C01B 32/194* (2017.08); *C07D 303/02* (2013.01); *C08J 5/005* (2013.01);
(Continued)

(58) Field of Classification Search
CPC ..... C08J 5/24; C08J 5/005; C08J 5/042; C08J 5/06; C08J 2300/00; C08J 2363/00;
(Continued)

(56) References Cited

U.S. PATENT DOCUMENTS 5,181,421 A   1/1993   Kline
7,832,983 B2  11/2010  Kruckenberg
(Continued)

FOREIGN PATENT DOCUMENTS

CN   102409528 A   4/2012
CN   103015157 A   4/2013
(Continued)

OTHER PUBLICATIONS

Fang et al. "Constructing hierarchically structured interphases for strong and tough epoxy nanocomposites by amine-rich graphene surfaces." Journal of Materials Chemistry, vol. 20, No. 43, Sep. 20, 2010, pp. 9635-9643.*

(Continued)

*Primary Examiner* — Holly C Rickman
*Assistant Examiner* — Lisa Chau
(74) *Attorney, Agent, or Firm* — Ostrager Chong Flaherty & Broitman P.C.

(57) ABSTRACT

Graphene fibers made from a graphene film formed into an elongated fiber-like shape and composite materials made from the graphene fibers. The graphene film has amine groups formed on at least an outer surface of the graphene film and epoxide groups formed on at least one edge of the graphene film. The amine groups are formed in a functionalized area on the outer surface of the graphene film that is within about 10 microns from the at least one edge of the graphene film, or the functionalized area may extend the entire width of the graphene film. The graphene film may also have holes formed through the graphene film. The elongated fiber-like shapes may be the graphene film in a rolled spiral orientation or the graphene film in a twisted formation.

26 Claims, 8 Drawing Sheets

(51) Int. Cl.
*C08J 5/06* (2006.01)
*C08J 5/00* (2006.01)
*C01B 32/194* (2017.01)
*C08K 7/06* (2006.01)
*C07D 303/02* (2006.01)
*D01H 1/14* (2006.01)
*D02G 3/02* (2006.01)
*D02G 3/06* (2006.01)

(52) U.S. Cl.
CPC . *C08J 5/06* (2013.01); *C08J 5/24* (2013.01); *C08K 7/06* (2013.01); *D01H 1/14* (2013.01); *D02G 3/02* (2013.01); *D02G 3/06* (2013.01); *C08J 2300/00* (2013.01); *C08J 2300/24* (2013.01)

(58) Field of Classification Search
CPC ..... C08J 2379/04; C08J 2379/08; C08K 9/04; D01F 9/12; D02G 3/38
See application file for complete search history.

(56) References Cited

U.S. PATENT DOCUMENTS

| | | | | |
|---|---|---|---|---|
| 8,361,321 | B2* | 1/2013 | Stetson | B01D 61/02 210/257.2 |
| 8,647,548 | B1 | 2/2014 | Humfeld | |
| 8,715,609 | B2 | 5/2014 | Humfeld et al. | |
| 2009/0124705 | A1* | 5/2009 | Meyer | A61K 33/44 514/769 |
| 2011/0017587 | A1* | 1/2011 | Zhamu | B82Y 30/00 204/157.62 |
| 2011/0052813 | A1* | 3/2011 | Ho | B82Y 30/00 427/256 |
| 2011/0281070 | A1 | 11/2011 | Mittal | |
| 2012/0077020 | A1 | 3/2012 | Muramatsu | |
| 2012/0298396 | A1 | 11/2012 | Hong et al. | |
| 2012/0330044 | A1 | 12/2012 | Hou et al. | |
| 2013/0034724 | A1* | 2/2013 | Sodano | B32B 7/04 428/325 |
| 2013/0164498 | A1 | 6/2013 | Langone | |
| 2014/0050920 | A1* | 2/2014 | Ray | D02G 3/16 428/368 |
| 2014/0121350 | A1 | 5/2014 | You et al. | |
| 2014/0308517 | A1 | 10/2014 | Zhamu et al. | |
| 2015/0004667 | A1 | 1/2015 | McKinney | |
| 2015/0031818 | A1 | 1/2015 | Moser | |
| 2015/0079340 | A1* | 3/2015 | Bullock | B32B 3/20 428/138 |

FOREIGN PATENT DOCUMENTS

| | | |
|---|---|---|
| CN | 103614902 A | 3/2014 |
| CN | 103396586 B | 11/2014 |
| JP | 2008248457 A | 10/2008 |
| KR | 101436500 B1 | 10/2014 |
| WO | 2007130979 A2 | 11/2007 |
| WO | 2012058553 A2 | 5/2012 |
| WO | 2012094634 A2 | 7/2012 |
| WO | 2012094634 A3 | 7/2012 |
| WO | 2013191809 A1 | 12/2013 |
| WO | 2014172619 A1 | 10/2014 |

OTHER PUBLICATIONS

Kuila et al., "Chemical functionalization of graphene and its applications" Progress in Materials Science 57 (2012) pp. 1061-1105.*
U.S.P.T.O. Office Action in co-pending U.S. Appl. No. 14/589,057 dated Nov. 20, 2015.
European Search Report in related application No. EP 15188442.6, dated Apr. 6, 2016.
Matei, Dan G. et al., "Functional Single-Layer Graphene Sheets from Aromatic Monolayers," Advanced Materials, 2013, 25, 4146-4151, Wiley-VCH Verlag GmbH & Co. KGaA, Weinhein, Germany.
Bhimanapati, Ganesh R., et al., "Heterogeneous Boron Nitride and Graphene Oxide: A New 2D Material System," Department of Materials Science and Engineering, Center for 2-Dimensional and Layered Materials, Penn State University, Pennsylvania, United States.
USPTO Office Action dated Jun. 23, 2016 in related U.S. Appl. No. 14/865,820.
European Search Report in related application No. EP 15188441.8, dated May 20, 2016, of The Boeing Company.
Database WPI, Week 201433, Thomson Scientific, London, GB; AN 2014-H03644, XP002757211, Shanghai Inst. Technology, Mar. 5, 2014.
Database WPI, Week 201474, Thomson Scientific, London, GB; AN 2014-U10828, XP002757154, Korea Inst. Machinery & Materials, Oct. 17, 2014.
Database WPI, Week 201251, Thomson Scientific, London, GB; AN 2012-E63084, XP002757212, Harbin Inst. Technology, Apr. 11, 2012.
Database WPI, Week 201370, Thomson Scientific, London, GB; AN 2013-P18120, XP002757215, Univ. Tianjin Polytechnic, Apr. 3, 2013.
Database WPI, Week 200876, Thomson Scientific, London, GB; AN 2008-M91181, XP002757213, Mitsui Bussan KK, Oct. 16, 2008.
European Search Report in related application No. EP 15188443.4, dated May 13, 2016, of The Boeing Company.
Federico, Bosia et al., "In Silico Tensile Tests and Design of Hierarchical Graphene Fibres and Composites," Physica Status Solidi. B, Basic Research, vol. 250, No. 8, Jul. 24, 2013, pp. 1492-1495.
Office Action dated Jul. 13, 2017 in U.S. Appl. No. 14/589,007.
Lin et al., Bulk Preparation of Holey Graphene via Controlled Catalytic oxidation, Nanoscale, 2013, 5, pp. 7814-7824.
Communication pursuant to Article 94(3) EPC in corresponding European Application No. 15 188 443.4, dated Jul. 18, 2018.
Non-Final Office Action dated Jun. 29, 2020 in U.S. Appl. No. 16/294,568.

* cited by examiner

GRAPHENE FIBER FOR AEROSPACE COMPOSITES

TECHNICAL FIELD

This disclosure generally relates to composite materials augmented with graphene, composite structures including component parts made from graphene-augmented composite materials, and methods for manufacturing graphene-augmented composite materials and composite structures with component parts made from graphene-augmented composite materials.

BACKGROUND

Composite materials are used in the manufacture of a wide variety of structures and component parts due to their high strength and rigidity, low weight, corrosion resistance and other favorable properties. For example, in the aerospace industry, composite materials are becoming widely used to manufacture aerospace structures and component parts for aerospace structures such as aircraft ribs, spars, panels, fuselages, wings, wing boxes, fuel tanks, tail assemblies and other component parts of an aircraft because they are lightweight and strong, and therefore provide fuel economy and other benefits. As used herein, the term "composite structure" means a structure that is manufactured, fabricated or assembled, in whole or in part, from one or more component parts made from composite materials (i.e., composite components) including, without limitation, aerospace structures.

One type of composite material commonly used in the aerospace industry is carbon fiber reinforced plastic ("CFRP"). CFRP generally comprises one or more composite layers or plies laminated together to form a sheet, laminate or layup. Each of the composite layers or plies comprises a reinforcement material and a matrix material. The matrix material surrounds, binds and supports the reinforcement material, and is generally a non-conductive polymer such as an epoxy resin. For aerospace applications, an aerospace grade resin is used as the matrix material, typically having four (4) epoxide groups in each epoxy monomer molecule to form multiple connections. The reinforcement material provides structural strength to the matrix material and the CFRP, and generally consists of strands of carbon fiber or carbon filaments, which are electrically conductive. Carbon fibers are typically formed as carbon tows comprising a defined number of carbon filaments. For aerospace applications, carbon tows may comprise bundles of carbon filaments ranging from about 1,000 to about 24,000 carbon filaments; carbon tows having up to about 300,000 carbon filaments may be used in other applications.

It is desirable to increase the amount of carbon in CFRP to further improve mechanical and/or electrical properties of composite structures without increasing weight or disturbing other desirable properties. But, simply increasing the amount of carbon fiber reinforcement material in CFRP does not meet this goal and is not cost efficient. Other forms of carbon, such as graphene, which has exceptional mechanical strength and thermal conductivity, would have beneficial effects in composite structures. Graphene is a hexagonal array of carbon atoms extending over two dimensions (i.e., it is one atom thick) that is typically produced in small flakes (or nanoplatelets). Each carbon atom in graphene is covalently bonded to three other carbon atoms, providing exceptional strength. However, mixing graphene into an epoxy resin comprising carbon fibers makes the epoxy resin weaker to strain in every direction because graphene will not bond with the carbon fibers and does not interact much with the epoxy resin.

Accordingly, there is room for improving the mechanical and electrical properties of composite structures and related methods for manufacturing composite structures that provide advantages over known composite structures and manufacturing methods.

SUMMARY

The foregoing purposes, as well as others, are achieved by integrating graphene fibers having an elongated fiber-like shape in the form of a rolled or twisted graphene sheet or film into CFRP composite materials as a supplement to or as a replacement for carbon reinforcement fibers. In a rolled form of the graphene fibers, the graphene film is rolled at a slight angle in an overlapping spiral orientation. Such a rolled graphene fiber may have a hollow core extending longitudinally through the rolled graphene fiber, or the rolled graphene fiber may be rolled to have no space in the center of the rolled graphene fiber.

In certain embodiments, the graphene film used to form graphene fibers may be functionalized with amine groups formed on an outer surface of the graphene film and epoxide groups formed on at least one edge of the graphene film. In an embodiment of the rolled form of the graphene fiber, the amine groups are formed in a functionalized area on the outer surface of the graphene film that is within about 10 microns from the at least one edge of the graphene film. In a twisted form of the graphene fiber, the amine groups may be formed anywhere on both surfaces of the graphene film.

Compared to traditional carbon fibers, the crystallinity of the disclosed graphene fibers is improved and is uniform through the graphene fiber instead of just on the surface as in a traditional carbon reinforcement fibers. This results in increased fiber cross-sectional area participating in load transfer and significantly higher modulus and strength. The optional hollow core rolled graphene fiber provides a graphene fiber with considerably less mass than traditional carbon fibers.

The disclosed graphene fibers may be used in the formation of composite materials, such as CFRP composite materials using standard equipment and processes for forming composite prepreg materials. The functionalization of the graphene film with amine groups on an outer surface of the graphene film and epoxide groups on at least one edge of the graphene film improves the interaction between the graphene fibers and the resin matrix material in the composite material to the point that the graphene fiber becomes part of the macromolecular resin complex.

In some embodiments, the graphene film used to form the graphene fiber has at least one hole positioned randomly in the graphene film. The at least one hole is substantially circular with a diameter of about 1-20 nanometers. In these embodiments, the entire outer surface of the graphene film may be functionalized with amine groups and all of the edges of the graphene film, including edges formed by the holes, may be functionalized with epoxide groups. That is, the functionalized area of the graphene film extends the entire width of the graphene film. Composite materials comprising these types of graphene fibers are macromolecules comprised of a base amine monomer (such as 44'DDS) and a base epoxy monomer (such as Bisphenyl F), which penetrates holes in the graphene film in the graphene fibers, and provides multiple connections between the graphene film and the resin matrix material in the composite material.

In accordance with a method of the disclosure, a method of increasing strength, stiffness and modulus of a composite material comprising reinforcement fibers and a matrix material is provided. Graphene fibers as disclosed herein are combined with a resin matrix material to form a prepreg material, and the prepreg material is cured to form the composite material with increased strength, stiffness and modulus.

Composite structures, including aerospace structures, comprising component parts made with composite materials having the disclosed graphene fibers, aircraft comprising such composite structures, and methods for making such composite structures are also considered to be within the scope of the present disclosure. Other objects, features, and advantages of the various embodiments in the present disclosure will be explained in the following detailed description with reference to the appended drawings.

DETAILED DESCRIPTION

In the following detailed description, various embodiments of graphene fibers and composite materials made with graphene fibers are described with reference to aerospace structures to illustrate the general principles in the present disclosure. It will be recognized by one skilled in the art that the present disclosure may be practiced in other analogous applications or environments and/or with other analogous or equivalent variations of the illustrative embodiments. For example, the graphene fibers and composite materials made with graphene fibers may be used in any industry that seeks the benefits of strong and light-weight materials. One of ordinary skill in the art will recognize and appreciate that the composite materials and related methods of increasing strength, stiffness and modulus in composite materials of the disclosure can be used in any number of applications involving such vehicles and structures. It should also be noted that those methods, procedures, components, or functions which are commonly known to persons of ordinary skill in the field of the disclosure are not described in detail herein.

Figure 1:
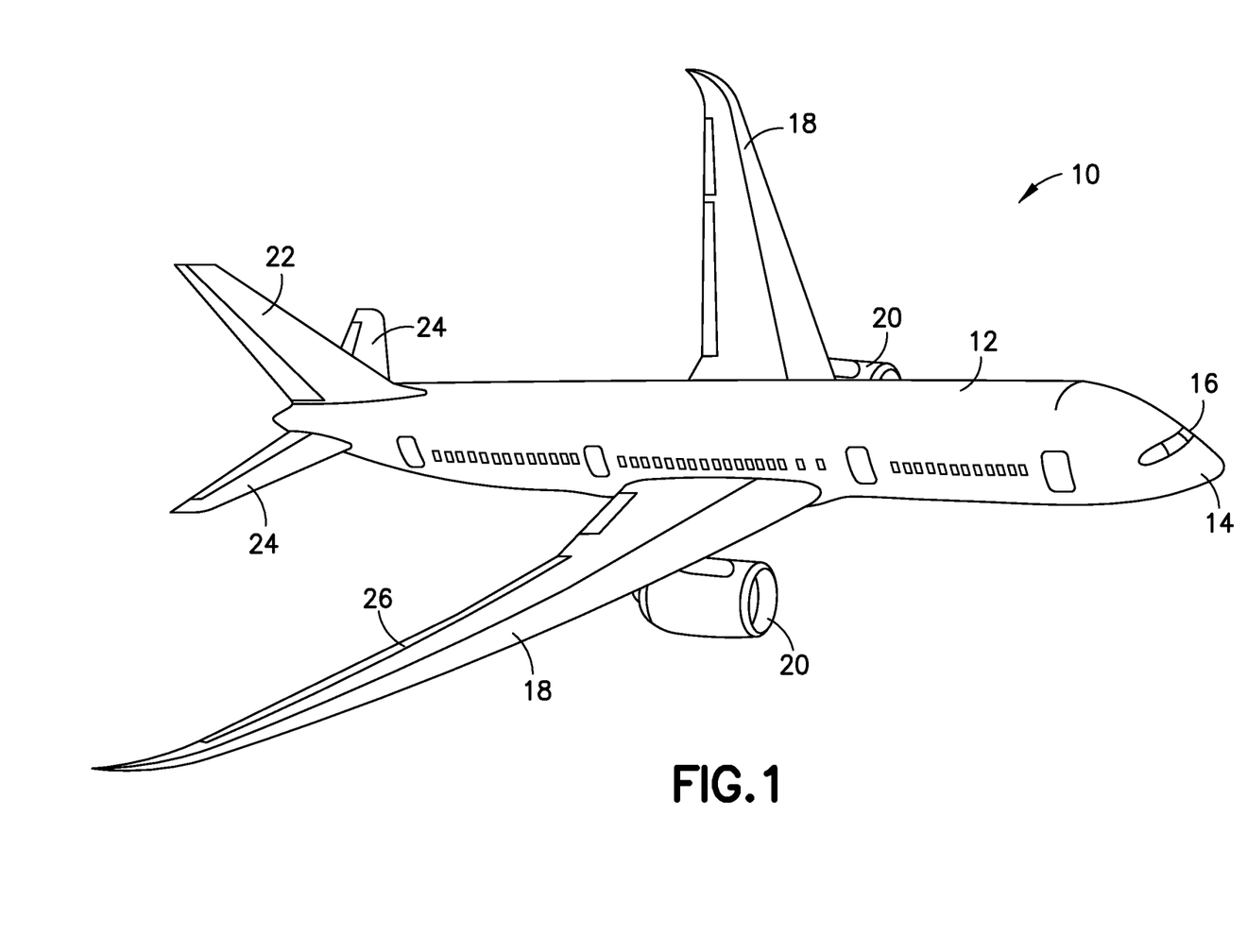
FIG. 1 is an illustration of a perspective view of an aircraft that may incorporate the composite materials disclosed herein.

Referring more particularly to the drawings, FIG. 1 is an illustration of a perspective view of an exemplary aircraft 10 that may incorporate a composite structure 26 comprising a composite material having graphene fibers in accordance with this disclosure. As shown in FIG. 1, the aircraft 10 comprises a fuselage 12, a nose 14, a cockpit 16, wings 18, one or more propulsion units 20, a vertical tail portion 22, and horizontal tail portions 24. Although the aircraft 10 shown in FIG. 1 is generally representative of a commercial passenger aircraft having one or more composite structures 26, the teachings of the disclosed embodiments may be applied to other passenger aircraft, cargo aircraft, military aircraft, rotorcraft, and other types of aircraft or aerial vehicles, as well as aerospace vehicles, satellites, space launch vehicles, rockets, and other aerospace vehicles, as well as boats and other watercraft, trains, automobiles, trucks, buses, or other suitable vehicles or items having composite structures.

Figure 2:
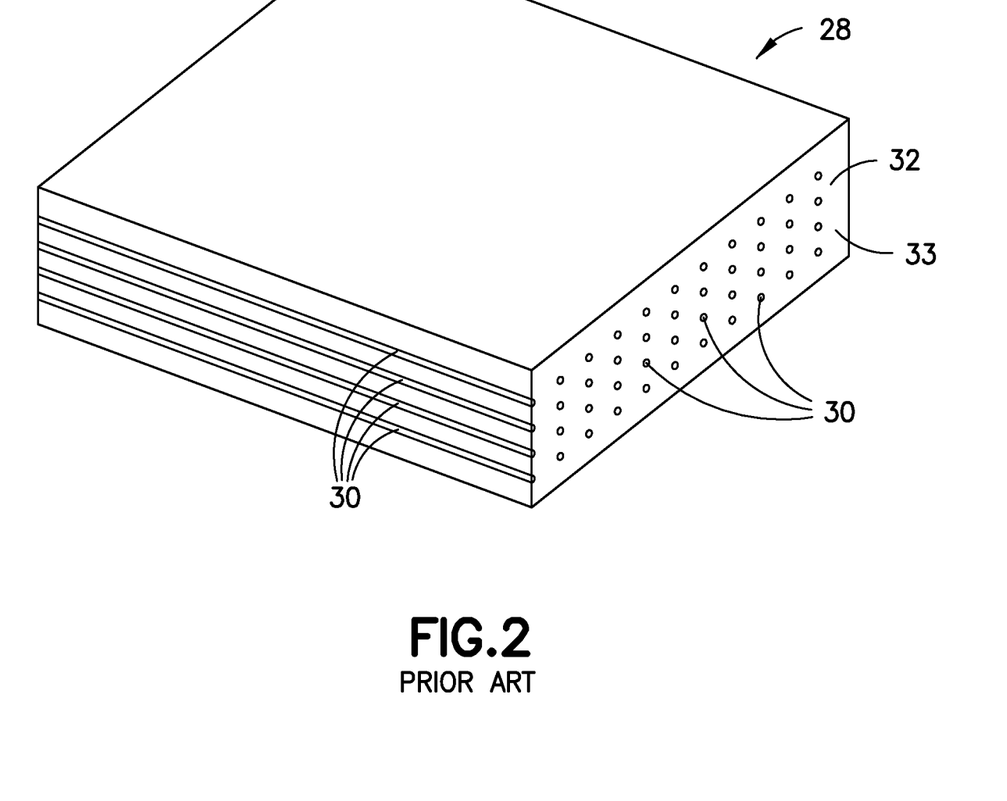
FIG. 2 is an illustration of a typical composite material comprising carbon reinforcement fibers and a matrix material.

The composite structures 26 may be any type of structure that is manufactured, fabricated or assembled, in whole or in part, from one or more component parts made from composite materials. An exemplary illustration of a typical CFRP-type of composite material 28 is shown in FIG. 2 comprising a single layer of carbon reinforcement fibers 30 impregnated with a matrix material 32. A typical process for making such a composite material 28 comprises combining hundreds of thousands of carbon reinforcement fibers 30 to form a bed of carbon reinforcement fibers 30, and then impregnating the bed with the matrix material 32. The matrix material 32 surrounds, binds and supports the carbon reinforcement fibers 30 and is generally a non-conductive polymer such as an epoxy resin 33. For aerospace applications, an aerospace-grade resin is used as the matrix material 32, having four (4) epoxide groups in each epoxy monomer molecule to form multiple connections. Typically, the molecules are tri- or tetra-functional epoxies and bifunctional amines. Since one component is at least tri-functional, the result of the extensive epoxy-amine chemical reaction is a dendrimeric structure, which provides strength and toughness greater than non-aerospace grade bi-functional epoxy resins. Aerospace-grade resins suitable for the composite materials of this disclosure include epoxy-amine resin systems having a cure temperature in the range of about 250° F. to 355° F. Examples of such resins include, but are not limited to, a toughened epoxy resin 3900-2 available from Toray Resin Company, a division of Toray Industries, Inc., Troy, Mich., and the CYCOM® 977-3 and CYCOM® 5320-1 curing resins available from Cytec Industries Inc., West Paterson, N.J.

In view of its exceptional properties, graphene has attracted tremendous research interest in recent years, particularly in the field of electronics. Graphene can now be made flawlessly or with controlled flaws in a molecular monolayer of unlimited length and width (i.e., it may be scaled for roll-to-roll processing), with grain size on the order of 100 nanometers. The controlled flaws can include amino-terminated groups (or amine groups) or other chemical functionalization with controlled density. Graphene may also be formed with holes having a predetermined size and location. In addition, graphene can now be oxidized by weak acids in whole or in part to form graphene derivatives, such as graphene oxide (GO) and reduced graphene oxide (rGO), having epoxide groups throughout the graphene, on part of the graphene, or only at its edges.

Figure 3:
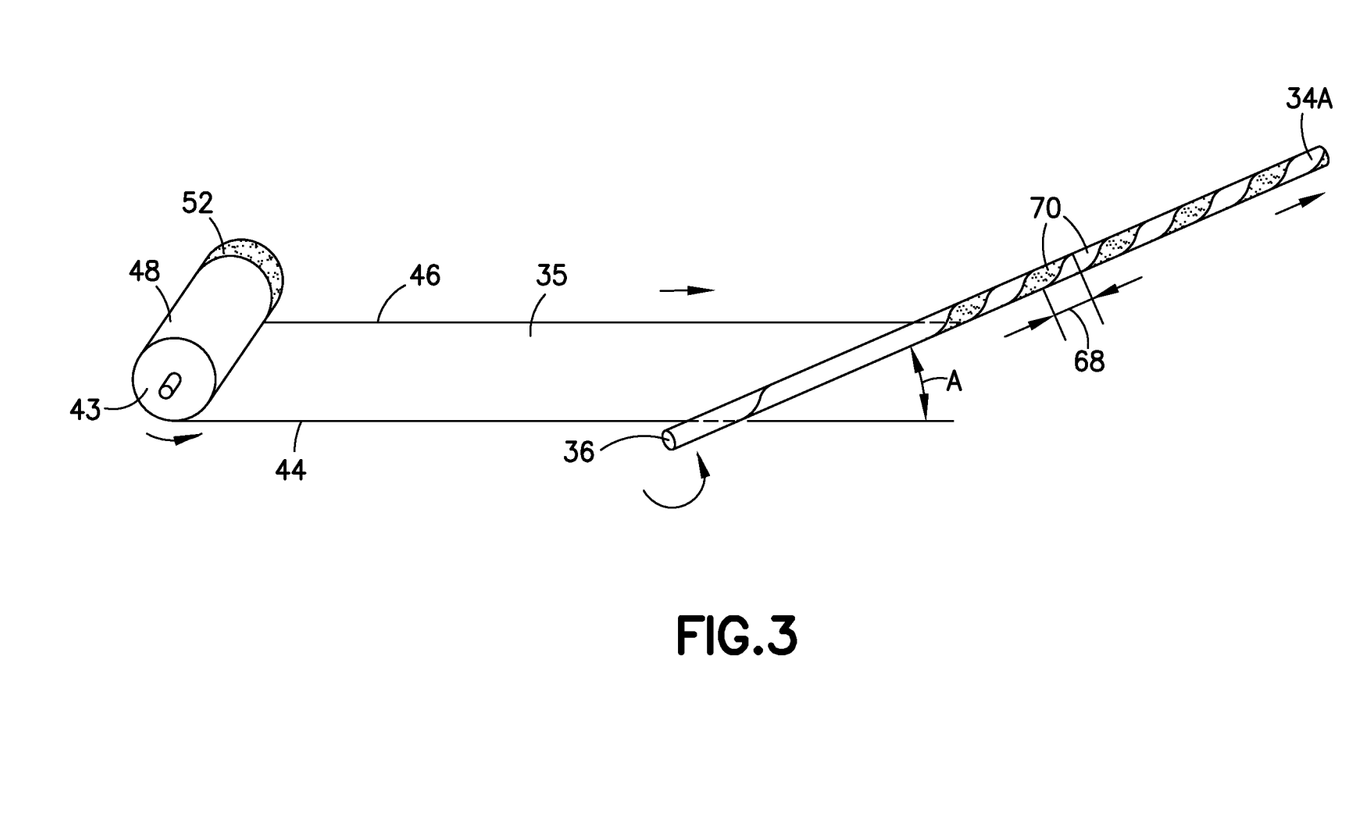
FIG. 3 is an illustration of one embodiment of a graphene fiber made by rolling a graphene sheet and exemplary equipment for producing a graphene fiber by rolling in accordance with this disclosure.
Figure 4:
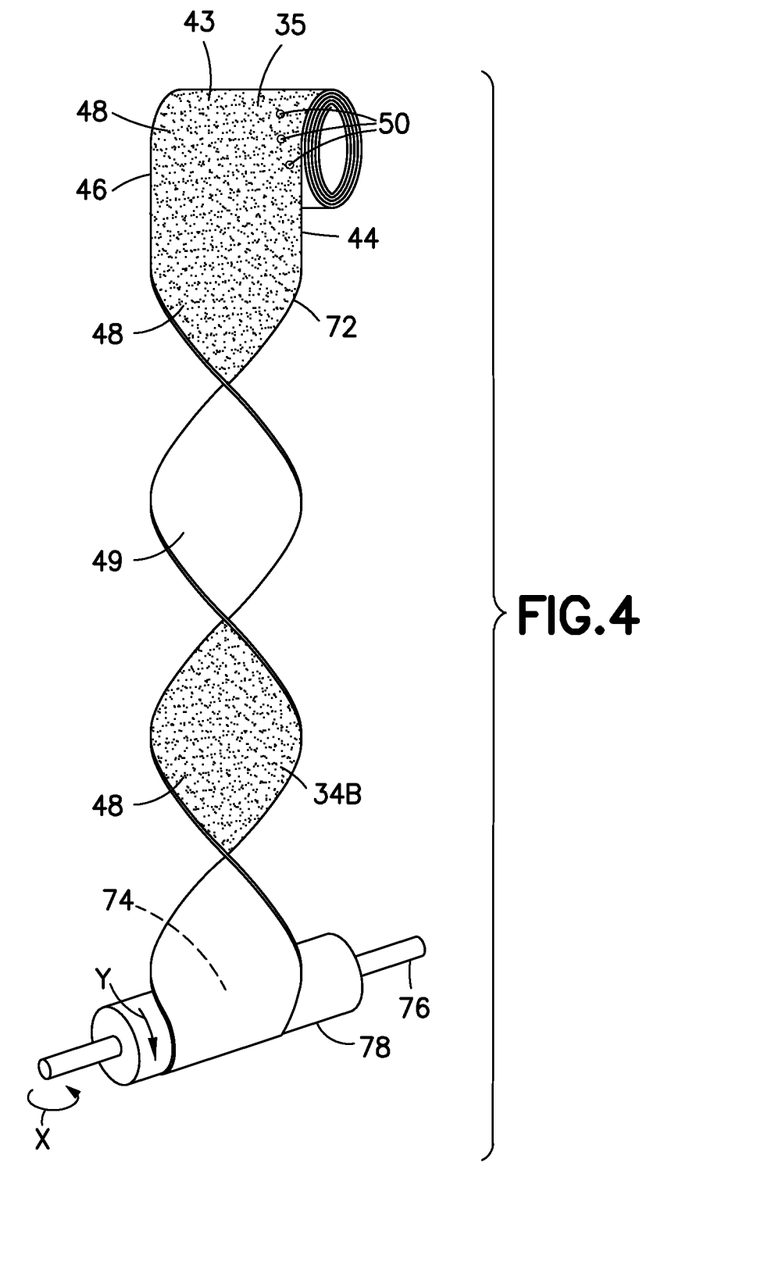
FIG. 4 is an illustration of another embodiment of a graphene fiber made by twisting a graphene sheet and exemplary equipment for producing a graphene fiber by twisting in accordance with this disclosure.

It has been determined that integrating graphene fibers 34A, 34B as disclosed herein, having an elongated fiber-like shape in the form of a rolled or twisted graphene film, into CFRP-type composite materials 28 (like the one shown in FIG. 2) as a supplement to or as a replacement for carbon reinforcement fibers 30 provides substantial benefits to the strength, stiffness and modulus of the composite materials 28. FIGS. 3-4 illustrate two exemplary embodiments of graphene fibers 34A, 34B, respectively, wherein a graphene film 35 is rolled at a slight angle A in an overlapping spiral orientation to form the elongated fiber-like shape of graphene fiber 34A (FIG. 3) or the graphene film 35 is twisted to form the elongated fiber-like shape of graphene fiber 34B (FIG. 4). These embodiments are further described below.

Figure 5:
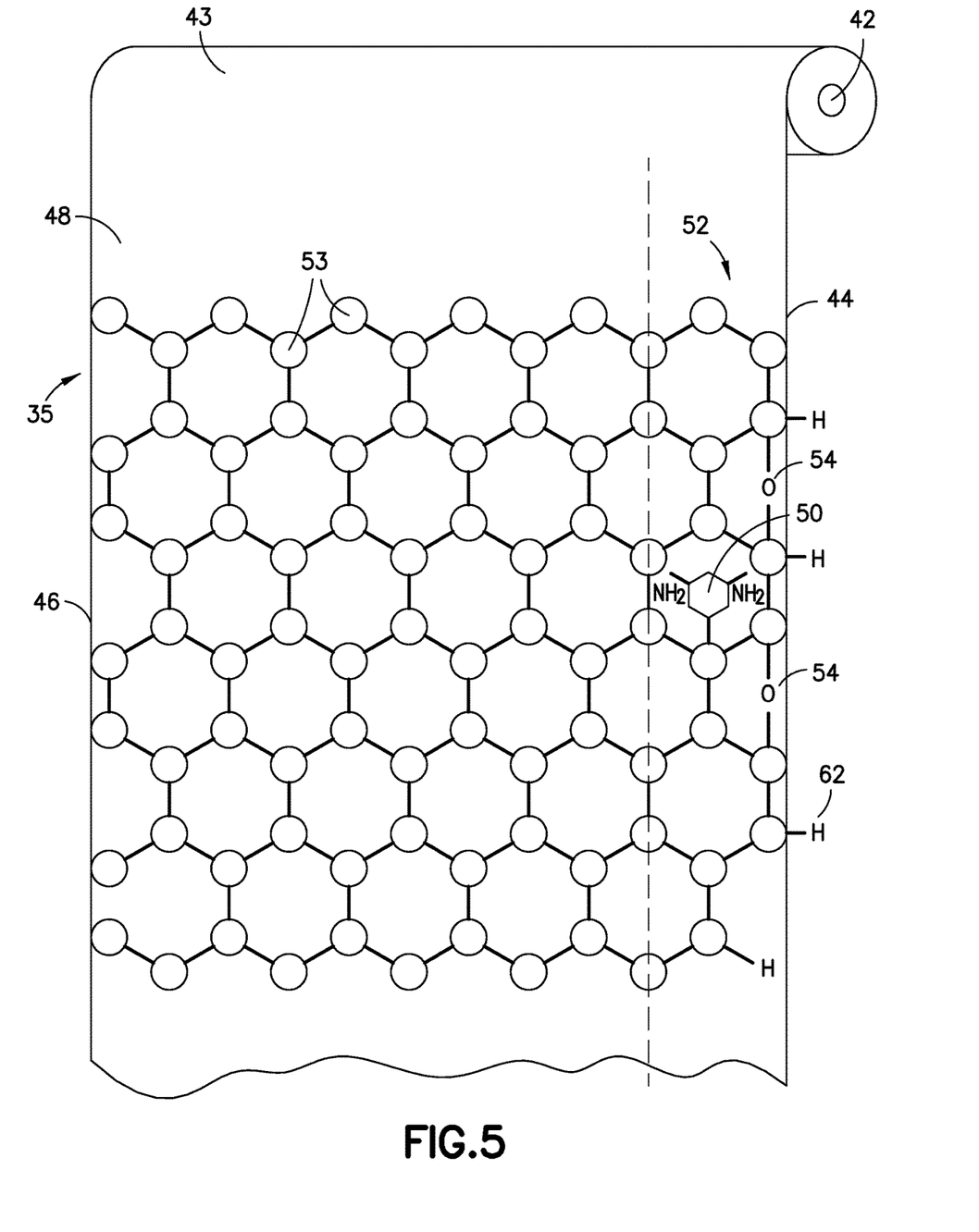
FIG. 5 is an illustration of one embodiment of a graphene film with amine group and epoxide group functionalization that may be used in the improved composite materials of this disclosure.

The graphene film 35 employed in all of the embodiments disclosed herein is formed as a long, thin graphene sheet having a width in the range of about 50 microns to about 500 microns from a first edge 44 to a second edge 46. The graphene film 35 may be rolled on a spool 42 for dispensing to form the graphene fibers 34A, 34B. The graphene film 35 may include functionalization on an outer surface 48 of the graphene film 35 and/or at one or both of the first edge 44 and the second edge 46. FIG. 5 is a blown-up illustration of a roll 43 of functionalized graphene film 35 wound on a spool 42 having added amine groups 50 in a functionalized area 52 on the outer surface 48 of the functionalized graphene film 35, and added epoxide groups 54 on the first edge 44 of the functionalized graphene film 35. The functionalized area 52 preferably extends the length of the graphene film 35 and up to about 10 microns in from the first edge 44. In other embodiments, the functional area 52 may extend the entire width of the graphene film 35 and have added epoxide groups 54 on all edges of the graphene film 35.

The amine groups 50 on the outer surface 48 of the graphene film 35 have a surface density of about 4.0E10 to about 2.0E12 groups per square millimeter (about 4.0E4 to about 2.0E6 groups per square micrometer or about 0.4 to about 2.0 groups per square nanometer) of the functionalized area 52. The surface density of amine groups 50 may also be described as about 0.1% to about 5.0% of carbon atoms 53 in the functionalized area 52 have amine groups 50 bonded thereto. That is, 1 to 50 carbon atoms 53 per 1,000 carbon atoms in the functionalized area 52 have an amine group 50 bonded thereto.

The graphene film 35 may be functionalized with amine groups 50 on the outer surface 48 by several methods including, for example, the methods disclosed in U.S. Publication No. 2014/0121350 A1 to YOU et al., published May 1, 2014, for preparing a polyimide-graphene composite material, and the method disclosed in Matei, Dan G. et al., "Functional Single-Layer Graphene Sheets from Aromatic Monolayers," *Advanced Materials*, 2013, 25, 4146-4151, WILEY-VCH Verlag GmbH & Co., Weinheim, Germany.

Figure 6:
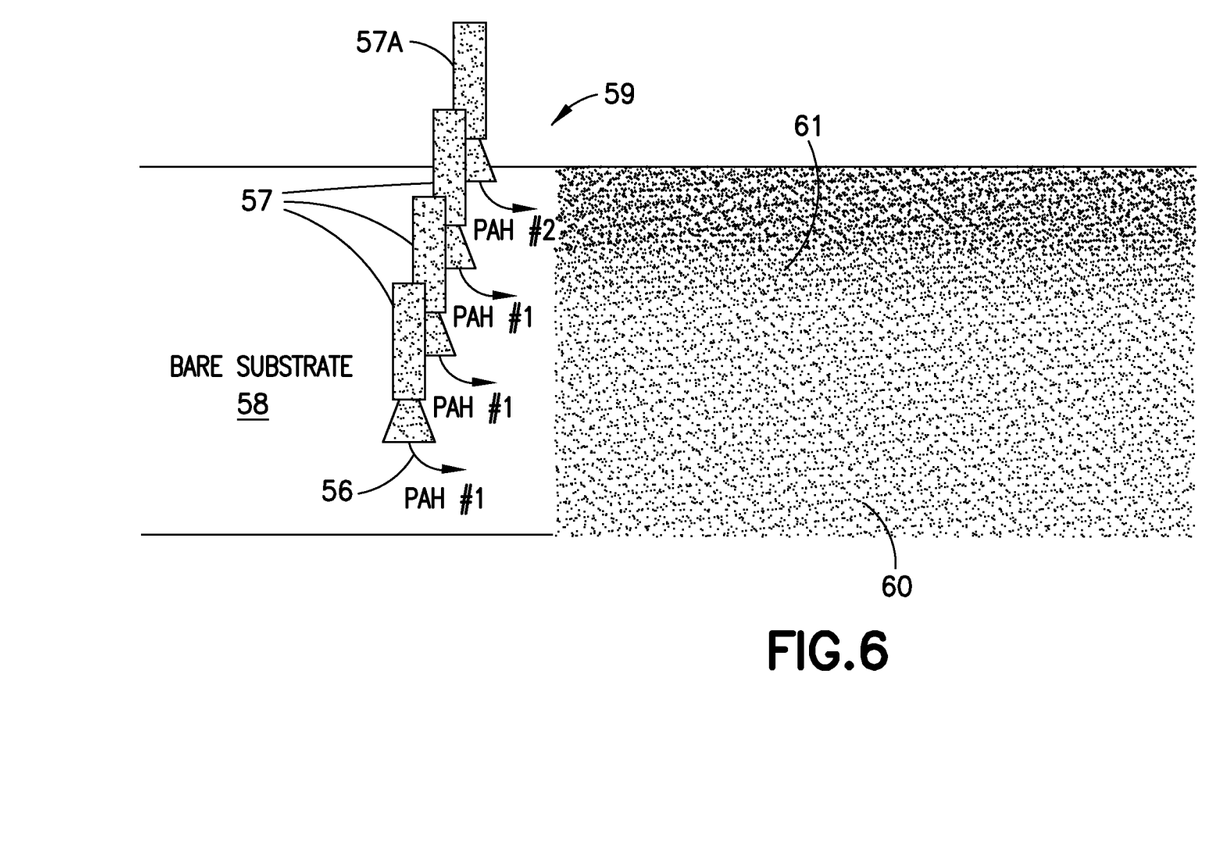
FIG. 6 is an illustration of exemplary equipment for producing a graphene film with amine group functionalization.

In one method of producing graphene film 35, illustrated in FIG. 6, polycyclic aromatic hydrocarbon (PAH) molecules 56 adsorb to a substrate 58, and the interactions of their aromatic rings cause them to form a self-assembled monolayer (SAM) 60. The remainder of each PAH molecule 56 beyond its first aromatic ring sticks up from the SAM 60. The PAH molecules 56 may be delivered to the substrate 58 via nozzles 57 arranged across a width of the substrate 58. By including a second species of PAH molecules with an amine group at some low concentration relative to the first PAH species, a SAM 60 with additional amine groups 50 can be formed. For example, one out of every 100 aromatic molecules may have an extra amine group 50 sticking up out of it. In FIG. 6, three of the four nozzles 57 deliver a first PAH species (PAH #1) and the fourth nozzle 57A positioned near one edge 59 of the substrate 58 delivers a second PAH species (PAH #2) so the amine groups 50 are positioned near the one edge 59, which becomes the first edge 44 in the graphene film 35. Some mixing occurs between the nozzles 57, 57A to form a gradient area 61 of increasing amine-functionalization toward the one edge 59. In other embodiments, any number of the nozzles 57 may deliver the second PAH species (PAH #2) to functionalize any width of the graphene film 35. The surface of the substrate 58 that the PAH molecules adsorb to becomes the outer surface 48 of the graphene film 35. Electron irradiation is used to induce bonds between the aromatic molecules at the substrate 58 to form a carbon nanomembrane (CNM). Temperature induced annealing in a vacuum or under protective atmosphere will complete the conversion of CNM into graphene.

Other methods of adding amine groups 50 may be used, and any type of amine structure may be added including, for example, 4,4' diamino diphenyl sulfone; 1-(4-aminophenyl)-1,3,3-trimethylindan-5-amine; N,N-bis(4-aminophenyl)benzene-1,4-diamine; 4,4'-methylenedianiline; 4,4'-oxydianiline; 3,3'-[1,3-phenylenebis(oxy)]dianiline; 4,4'-(9H-fluorene-9,9-diyl)dianiline; 4,4'[1,3-phenylenebis(oxy)]dianiline; 4,4'-methylenebis(2-ethylaniline); 3,3'-[(2,2-dimethylpropane-1,3-diyl)bis(oxy)]dianiline; 3,3'-[1,4-phenylenebis(methylene)]dianiline; 4,4'-sulfonylbis(N-methylaniline); 4,4'-[1,4-phenylenebis(oxy)]dianiline; 3,3'-sulfonyldianiline; aniline; 4,4'-(phenylphosphoryl)dianiline; 3-aminophenol; 4,4'-methylenedicyclohexanamine; 4,6-diethyl-2-methylbenzene-1,3-diamine; 2-(aminomethyl)-2,5,5-trimethylcyclohexanamine; 4,4'-thiodianiline; 2,2'-dimethylbiphenyl-4,4'-diamine; N-isopropyl-N'-phenylbenzene-1,4-diamine; N-(1,3-dimethylbutyl)-N'-phenylbenzene-1,4-diamine (Phenyl DMB); and N-cyclohexyl-N'-phenylbenzene-1,4-diamine (Phenyl CH).

Referring to FIG. 5, the graphene film 35 has a linear density of epoxide groups 54 formed on at least one of the first edge 44 and the second edge 46 of the graphene film 35, preferably on the side of the functionalized area 52, of about 7,000 to about 700,000 groups per millimeter (or about 0.007 to about 0.7 groups per nanometer, or about 7 to about 700 per micrometer). In other embodiments, all edges of the graphene film 35 may have a linear density of epoxide groups 54. The density of epoxide groups 54 may also be represented as about 0.1% to about 10% of carbon atoms at the first edge 44 of the graphene film 35 have epoxide groups 54 bonded thereto. That is, 1 to 100 carbon atoms 53 per 1,000 carbon atoms 53 has an epoxide group 54 bonded thereto.

Graphene film 35 may be functionalized with additional epoxide groups 54 by oxidation. Graphene, in general, can be oxidized by weak acids in whole or in part to form graphene derivatives, such as graphene oxide (GO) and reduced graphene oxide (rGO), having epoxide groups 54 throughout the graphene derivative, on part of the graphene derivative, or only at its edges. The weak acid would first attack the edges 44, 46 of the graphene film 35 where there are hydrogen terminations 62. The amount of oxidation is determined by the acid strength and exposure time. Examples of weak acids include formic acid, acetic acid and hydrogen sulfide. It is noted that "weak" does not mean that acid has a high pH. Instead, an acid is described as weak if it is only partially ionized in solution. Exposing the amine-functionalized graphene film 35 to a solution of formic acid for up to 30 minutes and then cleaning with ethanol may provide the desired density of epoxide groups 54.

Other methods of adding epoxide groups 54 may be used, and any type of epoxide structures may be added including, for example, 2,2'-[propane-2,2-diylbis(4,1-phenyleneoxymethylene) ]dioxirane; 2,2'-[methylenebis(4,1-phenyleneoxymethylene)]dioxirane; 2,2'-[methylenebis(2,1-phenyleneoxymethylene)]dioxirane; 2,2'-[ethane-1,1-diylbis(4,1-phenyleneoxymethylene)]dioxirane; phenyleneoxymethylene)[dioxirane; (Bis M); 4-(oxiran-2-ylmethoxy)-N,N-bis(oxiran-2-ylmethyl)aniline; 2,2'-[thiobis(4,1-phenyleneoxymethylene)]dioxirane; 2,2'-[sulfonylbis(4,1-phenyleneoxymethylene)]dioxirane; 2,2'-[butane-1, 4-diylbis(oxymethylene)]dioxirane; 3-(oxiran-2-ylmethoxy)-N,N-bis(oxiran-2-ylmethyl)aniline; 2,2'-oxybis (6-oxabicyclo[3.1.0]hexane); 2,2'-[1,4-phenylenebis (oxymethylene)]dioxirane; 2,2'-[prop-1-ene-1,2-diylbis (4,1-phenyleneoxymethylene)]dioxirane; 2,2'-[1,3'-]1,3-phenylenebis(oxymethylene)]dioxirane; 2,2'-[cyclohexane-1,2-diylbis(oxymethylene)]dioxirane; 2,2'-[(2,2-dichloroethene-1,1-diyl)bis(4,1-phenyleneoxymethylene)] dioxirane; 2,2'-[cyclohexane-1,4-diylbis (methyleneoxymethylene)]dioxirane; (Bis I); (Bis AF); (Bis Z); (Bis C); (Bis TMC); (Bis P); 2,2'-{propane-2,2-diylbis [(2,6-dibromo-4,1-phenylene)oxymethylene]}dioxirane; 7-oxabicyclo[4.1.0]hept-3-ylmethyl 7-oxabicyclo[4.1.0] heptane-3-carboxylate.

Figure 7:
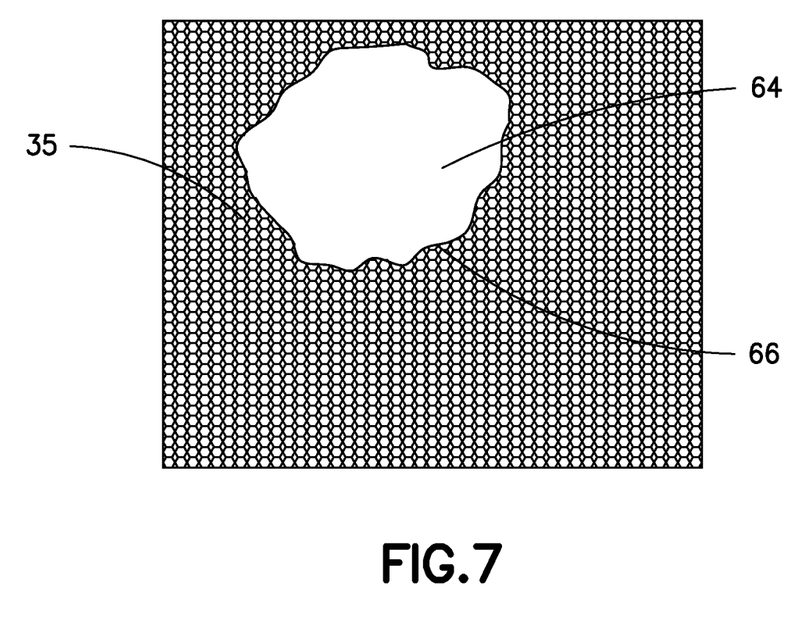
FIG. 7 is an illustration of a section of a graphene film that is functionalized with a hole.

Optionally, as shown in FIG. 7, graphene film 35 may be further functionalized by adding at least one hole 64 through the graphene film 35 to provide additional edges 66 where epoxide groups 54 can form. The at least one hole 64 may be formed by providing energy (such as with a laser) to remove molecules from the SAM prior to formation of the CNM, as disclosed herein. Preferably, the at least one hole 64 is formed in the graphene film 35 to have a substantially circular shape with a diameter of about 1-2 nanometers and a size of about 12-80 carbon atoms 37. That is, about 12-80 carbon atoms 53 are removed from the graphene film 35 to form the at least one hole 64 in the graphene film 35. The at least one hole 64 may be positioned in a random or predetermined pattern anywhere on the graphene film 35. The graphene film has a density of holes 64 in the range of about 4E7 to about 4E10 holes per square millimeter, or about 1 hole per 1,000 to 1 million carbon atoms. The holes 64 in the graphene film 35 provide space for molecules in, for example, a resin matrix material 32 to penetrate the holes 64 and be mechanically constrained by the graphene film 35, thereby further improving bonding capabilities.

Referring again to FIG. 3, the graphene film 35 is rolled in a spiral orientation to form a rolled graphene fiber 34A with an elongated fiber-like shape. Rolling may be achieved by any known method for rolling a film or sheet material. For example, a cylindrical pin 36 may be placed near one corner of the graphene film 35 and the graphene film 35 can then be rolled around the pin 36. Multiple layers of rolled graphene film 35 may be formed around the pin 36 by moving the roll 43 of the graphene film 35 longitudinally in both directions along the pin 36. The pin 36 is removed when a sufficient amount of graphene film 35 is rolled to form the desired diameter of the elongated fiber-like shape. The diameter of the rolled graphene fiber 34A is preferably in the range of about 1 micron to about 7 microns, and about 5 microns to about 7 microns for use aerospace applications. During the rolling process, tension should be applied to the graphene film 35 in the range of about 0.001 Newtons (N) per meter width of the graphene sheet. The pin used for rolling the graphene film 35 may be made with lithographic techniques to diameters down in the tens of nanometers. Preferably, the diameter of the pin is less than about 500 nanometers to form a center hollow area or core in the elongated fiber-like shape of the rolled graphene fiber 34A having a diameter of less than 500 nanometers. Other methods of rolling a film or sheet material may be used. For example, rolling methods with no pin may be used to form an elongated fiber-like shape with no center hollow area or core.

The spiral orientation of the rolled graphene film 35 is formed by rolling the graphene film 35 at an angle A relative to a longitudinal axis of the pin and overlapping layers of the graphene film 35. The angle A is preferably less than 0.6 degrees, which leads to a ratio of 1 width to 100 lengths. Rolling at an angle A nearer to zero (0) degrees is beneficial because the final diameter can be longer.

Successive layers of the graphene film 35 partially overlap previous wrapped layers of graphene film 35 such that the functionalized area 52 on the outer surface 48 of the graphene film 35 is not covered, and remains exposed. The offset distance 68 between adjacent overlaps 70 is determined by the angle A and the diameter of the rolled graphene film 35, which changes as it is rolled. In one example, a graphene fiber 34A has a final diameter of 5 microns, with the graphene film 35 rolled at an angle A of 0.6 degrees to provide an offset distance 68 between adjacent overlaps 70 of 50 microns.

In one embodiment of a rolled graphene fiber 34A, the graphene film 35 is functionalized on its outer surface 48 with amine groups 50 in the functionalized area 52 and epoxide groups 54 on the first edge 44 also in the functionalized area 52. The functionalized area 52 is within about 10 microns from the first edge 44. Holes 64 are not necessary for graphene film 35 in this embodiment. The wrapping process provides that the functionalized area 52 is on the outside of the graphene fiber 34A.

In another embodiment of a rolled graphene fiber 34A where the graphene film 35 is functionalized with at least one hole 64 positioned randomly in the graphene film 35, the entire outer surface 48 of the graphene film 35 may be functionalized with amine groups 50 and both the first edge 44 and the second edge 46 of the graphene film 35 may be functionalized with epoxide groups 54.

Referring again to FIG. 4, in another embodiment, the graphene film 35 is twisted to form a graphene fiber 34B with an elongated fiber-like shape having a twisted formation 72. Twisting may be achieved by any known method for twisting a film or sheet material, preferably a continuous process. In one embodiment, one end of the graphene film 35, such as the roll 43, may be supported with something stationary, and the free end 74 of the graphene film 35 may be supported with something that can rotate. For example, in a process that is continuous with the process that forms the graphene film 35, the graphene film 35 may be placed between a pair of rollers to apply a mechanical pressure on it, or between a surface and an air jet to stick the graphene film 35 to the surface so it cannot rotate. Referring to FIG. 4, once a good length of graphene film 35 is through the pair of rollers or past the air jet, the free end 74 of the graphene film 35 may be wrapped around a baton 76 and onto a spool or bobbin 78 that is coupled to the baton 76 for movement with the baton 76. The baton 76 and spool or bobbin 78 can then be rotated in the direction X as shown, for example, in FIG. 4 to twist the graphene film 35 to form the twisted formation 72 of the graphene fiber 34B while the spool or bobbin spins in the direction Y to pick up the graphene fiber 34B. The baton 76 may be rotated once or twice before the spool or bobbin 78 begins to spin. The graphene film 35 is preferably maintained at a tension of below 0.001N during the twisting process. Other types of rotating and spinning devices may be used. The twisted graphene fiber 34B has a diameter in the range of about 1 micron to about 7 microns, and about 5 microns to about 7 microns for use in aerospace composites.

In one embodiment of a twisted graphene fiber 34B, the graphene film 35 is functionalized on a first surface 48 with amine groups 50 in the functionalized area 52 and epoxide groups 54 on the first edge 44 also in the functionalized area 52. The functionalized area 52 is within about 10 microns from the first edge 44. Holes 64 are not necessary for graphene film 35 in this embodiment.

In other embodiments of a twisted graphene fiber 34B, the entire first surface 48 of the graphene film 35 may be functionalized with amine groups 50 and both the first edge 44 and the second edge 46 of the graphene film 35 may be functionalized with epoxide groups 54. In yet other embodiments, both the first surface 48 and the second surface 49 of the graphene film 35 may be functionalized with amine groups 50 in the functionalized area 52 or on the entire outer surface 48 and inner surface 49. The twisting process provides that the amine groups 50 are always exposed. Any of the foregoing embodiments of the twisted graphene fiber 34B may be further functionalized with at least one hole 64 positioned randomly in the graphene film 35, All of the foregoing embodiments of a rolled graphene fiber 34A and twisted graphene fiber 34B may be used to form a composite material 28 as shown in FIG. 2 the same way carbon reinforcement fibers 30 are used to form composite materials 28. Hundreds of thousands of rolled graphene fibers 34A or twisted graphene fibers 34B are combined together or with carbon reinforcement fibers 30 to form a bed of fibers, and the bed is impregnated with a resin matrix material 32 to form a composite prepreg, which can then be formed into a composite structure 26 and cured in accordance with known processes and equipment. In an embodiment, the rolled graphene fibers 34A or twisted graphene fibers 34B can be combined with carbon fibers to form a composite prepreg, which can then be formed into a composite structure 26 and cured in accordance with known processes and equipment.

Figure 8:
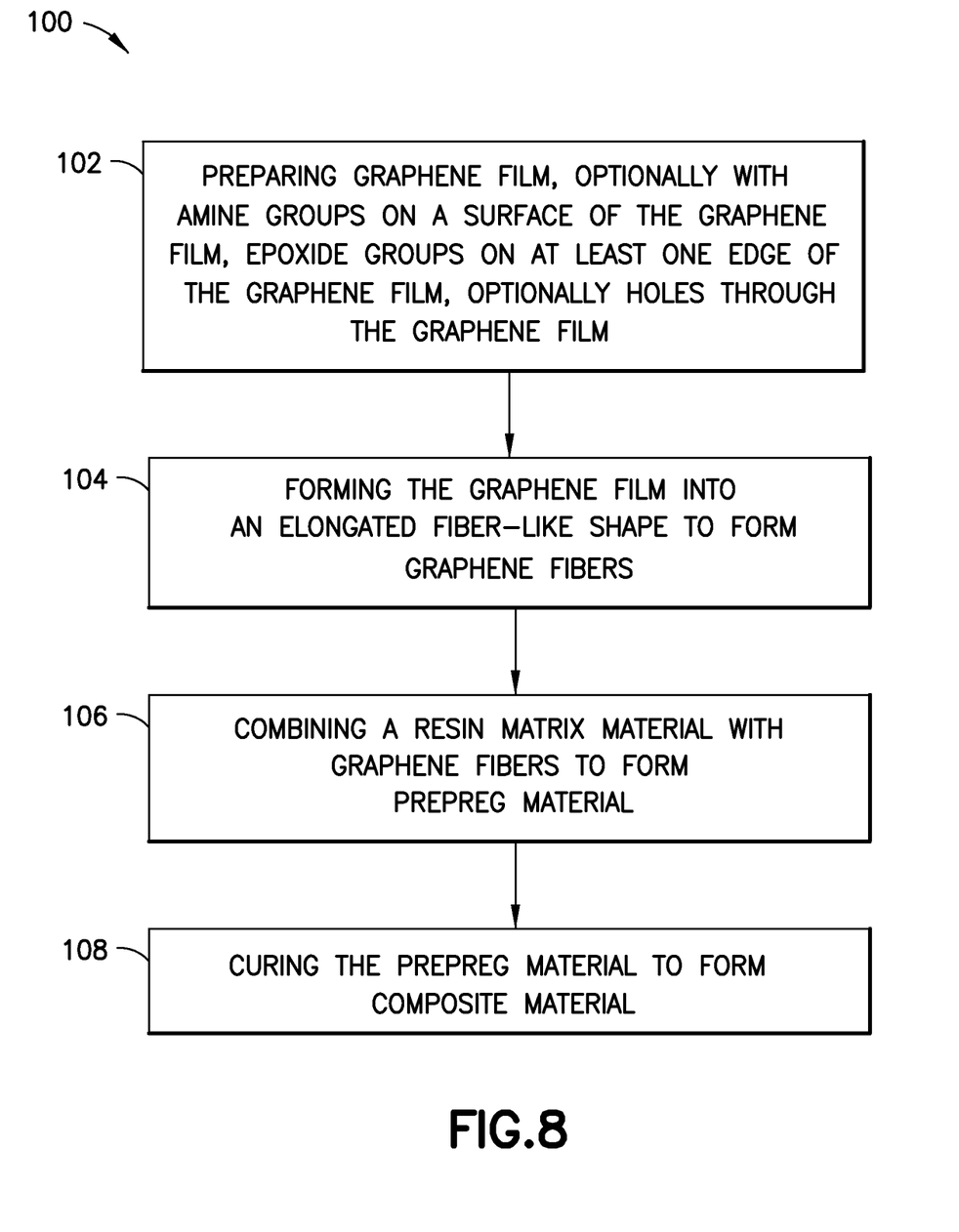
FIG. 8 is an illustration of a flow diagram of an exemplary method for fabricating a graphene fiber reinforced composite with increased strength, modulus and stiffness.

A flow diagram illustrating the steps of a method 100 of fabricating a graphene fiber reinforced composite with increased strength, modulus and stiffness 28 is shown in FIG. 8. The method 100 comprises step 102 of preparing a graphene film 35 optionally having amine groups 50 formed on an outer surface 48 of the graphene film 35, epoxide groups 54 formed on at least one of the first edge 44 and second edge 46 of the graphene film 35, and/or holes 64 formed through the graphene film 35 in accordance with the disclosure above.

In step 104, the graphene film 35 is formed into an elongated fiber-like shape to form either a rolled graphene fiber 34A (FIG. 3) or a twisted graphene fiber 34B (FIG. 4) in accordance with the disclosure above.

In step 106, a plurality of graphene fibers 34A, 34B are combined with a resin matrix material 32 to form a prepreg material. The prepreg material may comprise the graphene fibers 34A, 34B in unidirectional (aligned) or fabric (woven) form, impregnated to a desired amount with the resin matrix material 32. Preferably, the graphene fibers 34A, 34B are pre-impregnated with uncured resin matrix material 32 using equipment and processes known in the art for making prepreg materials. In step 108, the prepreg material is cured to form a composite material 28 using equipment and processes known in the art for curing prepreg materials.

Many other modifications and variations may of course be devised given the above description of various embodiments for implementing the principles in the present disclosure. For example, and without limitation, the same technology may be applied to fabric forms of prepreg materials where the graphene fibers are not aligned. It is intended that all such modifications and variations be considered as within the spirit and scope of this disclosure, as defined in the following claims.

The invention claimed is:

1. A graphene fiber comprising a single graphene film having a width in the range of about 50 microns to about 500 microns from a first edge to a second edge, the graphene film formed into an elongated fiber-like shape having a rolled spiral orientation with a diameter of about 1 to about 7 microns, the graphene fiber having amine groups bound to an outer surface of the graphene film only in a functionalized area on the outer surface that extends a length of the graphene film and about 10 microns in from the first edge of the graphene film and epoxide groups formed on the first edge of the graphene film, the amine groups in the functionalized area on the outer surface of the graphene film remaining exposed when the graphene film is in the rolled spiral orientation.

2. The graphene fiber of claim 1, wherein the graphene film has a linear density of epoxide groups formed on the first edge of about 7,000 to about 700,000 groups per millimeter.

3. The graphene fiber of claim 2, wherein the amine groups in the functionalized area on the outer surface of the graphene film have a surface density of about 4.0E10 to about 2.0E12 groups per square millimeter of the functionalized area.

4. The graphene fiber of claim 1, wherein about 0.1% to about 10% of carbon atoms at the first edge of the graphene film have epoxide groups bonded thereto.

5. The graphene fiber of claim 4, wherein about 0.1% to about 5.0% of carbon atoms in the functionalized area of the graphene film have amine groups bonded thereto.

6. The graphene fiber of claim 1, wherein the graphene fiber has a circumference of about 3 to about 22 microns.

7. The graphene fiber of claim 6, wherein the elongated fiber-like shape has a center hollow area having a diameter of less than 500 nanometers.

8. The graphene fiber of claim 7, wherein the spiral orientation comprises the single graphene film rolled at an angle greater than 0.0 degrees and less than 0.6 degrees and overlapping layers of the graphene film such that the functionalized area on the outer surface of the graphene film remains exposed.

9. The graphene fiber of claim 1, wherein the graphene film further comprises at least one hole formed through the graphene film.

10. The graphene fiber of claim 9, wherein the at least one hole is substantially circular and has a diameter of 1-2 nanometers.

11. The graphene fiber of claim 9, wherein the graphene film has a density of holes in the range of about 4E7 to about 4E10 holes per square millimeter, or about one hole per 1,000 to 1 million carbon atoms.

12. The graphene fiber of claim 9, wherein about 12-80 carbon atoms are removed from the graphene film to form each of the holes.

13. The graphene fiber of claim 9, wherein the amine groups on the outer surface of the graphene film have a surface density of about 4.0E10 to about 2.0E12 groups per square millimeter of the outer surface of the graphene film.

14. The graphene fiber of claim 13, wherein the graphene film has a linear density of epoxide groups formed on all edges of the graphene film of about 7,000 to about 700,000 groups per millimeter.

15. The graphene fiber of claim 13, wherein about 0.1% to about 10% of carbon atoms at all edges of the graphene film have epoxide groups bonded thereto.

16. A composite material comprising the graphene fiber of claim 1 and a matrix material.

17. A method of increasing strength of a composite material, the method comprising:
    forming a graphene fiber comprising a single graphene film having a width in the range of about 50 microns to about 500 microns from a first edge to a second edge, the graphene fiber formed into an elongated fiber-like shape having a rolled spiral orientation with a diameter of about 1 to about 7 microns, the graphene fiber having amine groups bound to an outer surface of the graphene film only in a functionalized area on the outer surface that extends a length of the graphene film and about 10 microns in from the first edge of the graphene film and epoxide groups formed on the first edge of the graphene film, the amine group in the functionalized area on the outer surface of the graphene film remaining exposed in the fiber-like shape;
    combining a matrix material with a plurality of the graphene fibers to form a prepreg material; and
    curing the prepreg material to form the composite material.

18. The method of claim 17, wherein the step of forming the graphene fiber further comprises forming the graphene fiber with a circumference of about 3 to about 22 microns, and a center hollow area having a diameter of less than 500 nanometers.

19. The method of claim 17, wherein the step of forming the graphene fiber further comprises maintaining a tension in the graphene film at about 0.001 N per meter of film width.

20. The method of claim 17, wherein the step of forming the graphene fiber further comprises forming at least one hole in the graphene film.

21. The method of claim 20, wherein the at least one hole is formed in a substantially circular shape with a diameter of 1-20 nanometers.

22. The method of claim 21, wherein the graphene film has a density of holes in the range of about 4E7 to about 4E10 holes per square millimeter, or about one hole per 1,000 to 1 million carbon atoms.

23. The method of claim 17, further comprising combining carbon fiber with the graphene fiber to form the prepreg material.

24. A graphene fiber comprising a single graphene film having a width in the range of about 50 microns to about 500 microns from a first edge to a second edge, the graphene film formed into an elongated fiber-like shape, the graphene film having amine groups bound to an outer surface of the graphene film only in a functionalized area on the outer surface that extends a length of the graphene film and about 10 microns in from the first edge of the graphene film and remaining exposed in the elongated fiber-like shape, and epoxide groups formed only at the first edge of the graphene film.

25. The graphene fiber of claim 24, wherein the elongated fiber-like shape comprises the graphene film in a rolled spiral orientation comprising the graphene film rolled at an angle greater than 0.0 degrees and less than 0.6 degrees.

26. The graphene fiber of claim 24, wherein the first edge of the graphene film that is within the functionalized area has a linear density of epoxide groups of about 7,000 to about 700,000 groups per millimeter, such that about 0.1% to about 10% of carbon atoms at the first edge of the graphene film have epoxide groups bonded thereto, and the outer surface of the graphene film that is within the functionalized area has a surface density of amine groups of about 4.0E10 to about 2.0E12 groups per square millimeter of the functionalized area, such that about 0.1% to about 5.0% of carbon atoms in the functionalized area of the graphene film have amine groups bonded thereto.

* * * * *